United States Patent
Huttner et al.

(10) Patent No.: US 10,092,168 B1
(45) Date of Patent: Oct. 9, 2018

(54) LIGHTED MEDICAL INSTRUMENT

(71) Applicant: Bionix Development Corporation, Toledo, OH (US)

(72) Inventors: James J. Huttner, Sylvania, OH (US); Josh Noble, Oak Harbor, OH (US)

(73) Assignee: Bionix Development Corporation, Toledo, OH (US)

( * ) Notice: Subject to any disclaimer, the term of this patent is extended or adjusted under 35 U.S.C. 154(b) by 0 days.

(21) Appl. No.: 15/669,009

(22) Filed: Aug. 4, 2017

Related U.S. Application Data

(63) Continuation of application No. 12/856,745, filed on Aug. 16, 2010, now abandoned.

(60) Provisional application No. 61/274,402, filed on Aug. 17, 2009.

(51) Int. Cl.
| | | |
|---|---|---|
| *A61B 1/06* | (2006.01) | |
| *A61B 1/00* | (2006.01) | |
| *A61B 1/07* | (2006.01) | |
| *A61B 1/313* | (2006.01) | |

(52) U.S. Cl.
CPC ...... *A61B 1/00165* (2013.01); *A61B 1/00087* (2013.01); *A61B 1/00096* (2013.01); *A61B 1/0684* (2013.01); *A61B 1/07* (2013.01); *A61B 1/313* (2013.01)

(58) Field of Classification Search
CPC . A61B 18/1445; A61B 17/28–17/2841; A61B 17/29; A61B 1/06–1/0669
See application file for complete search history.

(56) References Cited

U.S. PATENT DOCUMENTS

| | | | | |
|---|---|---|---|---|
| 1,965,865 A | * | 7/1934 | Thompson | A61B 1/0669 246/1 C |
| 3,357,423 A | * | 12/1967 | Winchester | A61B 1/00117 385/107 |
| 4,499,898 A | * | 2/1985 | Knepshield | A61B 17/3211 30/320 |
| 5,282,806 A | * | 2/1994 | Haber | A61B 17/29 606/139 |
| 5,489,290 A | * | 2/1996 | Furnish | A61B 17/29 600/564 |
| 5,529,570 A | * | 6/1996 | Storz | A61B 1/07 600/185 |
| 5,548,676 A | * | 8/1996 | Savage, Jr. | G02B 6/32 385/88 |

(Continued)

*Primary Examiner* — Eduardo C Robert
*Assistant Examiner* — Michelle C Eckman
(74) *Attorney, Agent, or Firm* — Marshall & Melhorn, LLC

(57) ABSTRACT

A light transmitting medical instrument provides for the enhanced performance of medical procedures. The light transmitting medical instrument comprises a light pipe having a first end operatively coupled to a light source and a second end having a functional tip having at least two arms. A sliding closure sleeve is mounted about the light pipe. The sliding closure sleeve has a first end portion at which the sliding closure sleeve is fixed to the light pipe in a manner such that relative movement therebetween is prevented and a second end proximate the functional tip of the light pipe. The sliding closure sleeve further comprises a spring-like actuator finger grip that, when forced radially inward, causes the second end of the sliding closure sleeve to move toward the functional tip, thereby forcing the arms of the functional tip towards one another.

14 Claims, 4 Drawing Sheets

(56) References Cited

U.S. PATENT DOCUMENTS

| | | | | |
|---|---|---|---|---|
| 5,607,449 A * | 3/1997 | Tontarra | ............... | A61B 17/29 606/205 |
| 5,620,456 A * | 4/1997 | Sauer | ............... | A61B 17/3417 604/164.01 |
| 5,732,176 A * | 3/1998 | Savage, Jr. | ............. | G02B 6/32 385/88 |
| 5,782,748 A * | 7/1998 | Palmer | ................. | A61B 10/06 600/104 |
| 5,928,137 A * | 7/1999 | Green | ................ | A61B 1/00052 600/104 |
| 6,187,026 B1 * | 2/2001 | Devlin | ............... | A61B 17/2909 606/205 |
| 6,488,695 B1 * | 12/2002 | Hickingbotham | ........................ A61B 17/2909 | 606/206 |
| 6,730,076 B2 * | 5/2004 | Hickingbotham | ..... | A61B 90/36 606/13 |
| 6,758,824 B1 * | 7/2004 | Miller | ................ | A61B 10/025 600/566 |
| 8,177,728 B2 * | 5/2012 | Hibner | ............... | A61B 10/0275 600/567 |
| 8,882,750 B2 * | 11/2014 | Stefan | .................... | A61B 17/29 606/1 |
| 2002/0087050 A1 * | 7/2002 | Rudischhauser | ...... | A61B 1/267 600/199 |
| 2002/0156344 A1 * | 10/2002 | Pasricha | ............ | A61B 1/0014 600/113 |
| 2004/0267275 A1 * | 12/2004 | Cournoyer | ......... | A61B 17/7086 606/99 |
| 2005/0143626 A1 * | 6/2005 | Prescott | ............. | A61B 1/00087 600/162 |
| 2006/0048787 A1 * | 3/2006 | Manzo | ............... | A61B 17/3201 128/898 |
| 2007/0100210 A1 * | 5/2007 | Selover | ................. | A61B 17/02 600/199 |
| 2008/0154277 A1 * | 6/2008 | Machalk | ........... | A61B 17/7091 606/99 |
| 2010/0125172 A1 * | 5/2010 | Jayaraj | .................... | A61B 1/06 600/249 |
| 2010/0292724 A1 * | 11/2010 | Ravikumar | .......... | A61B 17/221 606/185 |

* cited by examiner

LIGHTED MEDICAL INSTRUMENT

BACKGROUND OF THE INVENTION

A number of medical procedures require the combination of illumination and visualization to enable the physician to properly carry out that procedure. Body orifices and cavities are dark, covered by opaque skin and contain deep and complex recesses. Without being able to adequately visualize the tissues, the doctor is literally "in the dark", and the patient may be at risk. It is therefore advantageous that instruments and devices created to perform these procedures be able to provide bright illumination at their site of action, improving the experience for the doctor and enhancing the outcome for the patient.

One such procedure is laparoscopic surgery. Laparoscopic surgery is a method of minimally invasive surgery that allows surgical procedures to take place without the large incisions typically used in such surgeries. In a laparoscopic procedure, the surgeon makes a relatively small (0.5 to 1.0 cm) incision in the abdomen, usually through the navel. A trocar, a hollow tube with a gas-sealable port, is placed in the incision, and air or carbon dioxide gas is introduced into the abdominal cavity to inflate the abdomen, moving the abdominal wall away from the internal organs by means of gas pressure. One or more other small incisions are made, also using a gas-sealable port, through which various instruments—graspers, needle holders, electrocautery units, and the like—may be placed to allow the surgeon to complete the procedure. Because the overall procedure takes place within a closed abdominal cavity, the surgeon must view the work directly through a laparoscope—a surgical telescope—or indirectly on a monitor, with the image transmitted from a small camera inserted into through the trocar incision. Illumination must be provided via one or more fiberoptic probes that are usually also inserted through the trocar site.

The need for illumination to enhance visualization of the laparoscopic procedures cannot be overstressed. Often, various organs or body structures can impede the illumination of an operative site removed from the light field cast by the trocar illuminator. In those cases, the illuminator must be manipulated or reinserted to achieve sufficient illumination of the operative site to allow the procedure to continue. This may take time, and it may be difficult or impossible in some instances. Clearly, any device or strategy that would enhance the illumination of the operative site would improve the safety and efficiency of the procedure.

Current laparoscopic instruments do not provide for illumination to be directed to the operative site. They are generally made from opaque stainless steel and plastic components, and will not transmit light. Because of their necessary small diameter, it is not practical to incorporate wires and bulbs into these instruments. Also, issues of patient safety including overheating and electrical safety preclude the incorporation of bulbs and most wiring into these instruments.

Another example of a procedure that would benefit from directed illumination is foreign body removal. A common problem in pediatric medicine is the retrieval of objects from the nose and ears. Referred to in the literature as foreign bodies, they are placed in their nares or ear canals by children as part of their normal inquisitive natures and play. These foreign bodies are most often objects found close at hand to the child—stones, beads, beans, buttons, and smallish bits of organic matter such as paper or foam rubber. By the nature of the ear canal and nares, these objects tend to be rounded or oblong in shape and usually small, although occasionally the size of an object may be surprising. Other important foreign bodies are those that find their way into the ear or nose by accident, such as insects, which can cause significant anxiety and pain until they are removed.

It is generally important to remove foreign bodies when found in the ears or nose for several reasons. Foreign objects in the nose pose a danger of airway obstruction should they be inhaled through the nasopharynx into the lungs. Aspiration of a foreign body in this fashion should always be considered in the case of nasal foreign objects, and an attempt to retrieve the object or ensure its absence is imperative. Also, foreign bodies in the ear canal can cause irritation and pain. Left alone, they can erode into the wall of the ear canal where they may become embedded, requiring a surgical approach for their removal. Foreign bodies can also obstruct the ear canal, causing water retention and subsequent external otitis. For these reasons, foreign bodies found in the ear canal must also be removed.

Removing foreign bodies from either the nose or ears is not a trivial undertaking, and many approaches and devices have been used and designed to accomplish this task. The first and usually simplest approach has been to use a pair of forceps or tweezers to reach in and grasp the foreign object, and then pull it out. Both straight and offset bayonette forceps have been used for this task. While generally successful, forceps have limitations especially with round objects, such as beads. As they close, the squeezing action may force the bead deeper into the passage, much like squirting a watermelon seed between one's fingers. Thus, forceps tend to be used more for organic and irregularly shaped objects like paper and insects, and less for roundish beans and beads.

Another approach has been the use of suction, introduced by means of a narrow rigid tube, and often with a soft, formable tip. The tip is placed against the foreign object and the vacuum is applied. The tube is then withdrawn along with the foreign body. This method works best with hard, smooth objects like beads, and less well with porous materials such as paper and insects. Also, the suction tip is not lighted, so this represents a blind procedure. It is possible during the introduction of the tube into the passage (ear canal or nose) to inadvertently shove the foreign body deeper into the passage.

Another method that has been developed is the use of a balloon catheter. This is realistically only an option for the nose, due to size constraints. In this method, a balloon catheter is passed behind the foreign body in its deflated state. The balloon is then inflated with air, and the catheter is withdrawn. If successful, the balloon will push the foreign body out of the passage as it is withdrawn. Again, this tends to be a blind procedure, although the relatively larger size of the nares allows for better lighting and visualization.

In the ear, due to the narrow confines of the ear canal, the use of a balloon catheter is not practical. However, a similar approach is often used employing an ear curette to reach behind the foreign object and pull it out. While often successful, this approach sometimes leads to trauma and pain in the external ear canal. Other methods have also been utilized to remove foreign bodies. These methods, such a needles and superglue, have found their way into the medical literature but are not readily commercializable, nor are they appropriate for all cases.

SUMMARY OF THE INVENTION

This invention relates to a light transmitting medical instrument for the enhanced performance of various medical procedures. The light transmitting medical instrument of the invention comprises a light pipe having a first end operatively coupled to a light source and a second end having a functional tip having at least two arms. A sliding closure sleeve is mounted about the light pipe. The sliding closure sleeve has a first end portion at which the sliding closure sleeve is fixed to the light pipe in a manner such that relative movement therebetween is prevented and a second end proximate the functional tip of the light pipe. The sliding closure sleeve further comprises a spring-like actuator finger grip that, when forced radially inward, causes the second end of the sliding closure sleeve to move toward the functional tip, thereby forcing the arms of the functional tip towards one another.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

Figure 1:
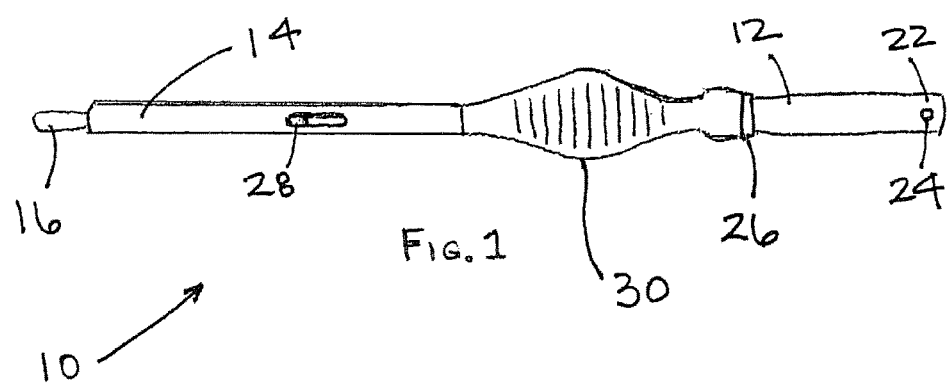
FIG. 1 shows a side view of a light transmitting medical instrument in accordance with the invention.

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

In a preferred embodiment, the present invention is a device designed to remove a foreign body from either the nose or the ear canal under direct visualization. The device uses a curved grasper that can be closed so that its tips are in opposition, enclosing and holding a foreign object whether it is round, flat, or irregularly shaped. The grasper forms the distal portion of a light pipe, which transmits significant light from a lightweight LED source into the passage. A magnification lens may be provided to allow the operator to visualize the tip of the grasper, and, in conjunction with the illumination, provides direct visualization of the procedure. The device has a non-lighted sleeve that surrounds the light pipe. This sleeve is tethered to the light pipe at its proximal end, but is otherwise not attached to the light pipe and is free to move. A pair of finger grips forms a spring-like mechanism between the tethered end and the sliding portion of the sleeve. To close the grasper, the operator squeezes the spring-like finger grips. This forces the distal portion of the sleeve to slide toward the grasper. As the sleeve slides over the spread arms of the grasper, it forces the grasper arms together, producing a strong gripping action. The grasper arms are preferably slightly curved, and they can enclose round objects like beads and still grip flat or irregularly shaped objects. With the grasper firmly holding the foreign body, the entire device is withdrawn from the nose or ear along with the foreign object.

The invention discloses a design for medical instruments that are constructed from light conductive plastics that allow them to act as light pipes to transmit light directly onto the procedure site. The light can come from an attached fiberoptic cable, from an attached battery powered light source, or other suitable source. In each case, the light is transmitted from the light source end to the functional tip of the device, and from there projected onto the operative site. Depending on their intended use, the functional tips of the devices may take many forms. For example, they may be graspers for foreign body retrieval, or cutting and cauterizing tips for laparoscopic surgery. Other functional tip styles are also possible. Because of their design, the instruments in accordance with the current invention are generally intended to be single use devices. They may be coupled with a reusable handle system, or they may be entirely constructed for single use.

The current invention represents an improvement over currently available medical instruments. The lighted instrument 10 as shown in the drawings is comprised of a light pipe 12 and a sliding closure sleeve 14 that work together to close and keep closed the surgical tips 16 at the distal end of the device, and a handle portion 18. The surgical tips 16 can be molded in a variety of configurations, so as to serve as graspers, needle holders, probes, scissors, electrocautery tips, and other functional end units routinely used in laparoscopic surgery.

The lighted medical instrument 10 as shown has two main portions, a light pipe 12 and a sliding closure sleeve 14, that work together to close and keep closed the functional tips 16 at the distal end of the device. The functional tips 16 comprise the distal end of the light pipe portion 12, and can be molded in a variety of configurations, so as to serve as graspers, needle holders, probes, scissors, electrocautery tips, and other functional end units routinely used in various medical procedures. The two parts—light pipe 12 and sliding closure sleeve 14—are assembled to create the device. In use, the device is affixed to a source of illumination 20, such as a bright white light-emitting diode (LED) or fiberoptic light source that provides light that is transmitted down the light pipe 12 to the functional tips 16, illuminating the procedure site. Magnification and optics may be added to the device, either permanently or removably affixed, to improve visualization.

The light pipe portion 14 of the device 10 is comprised of a transparent light conducting member, preferably made from a plastic material with low haze and high transparency. The desired functional tips 16 are molded onto the distal end of the light pipe 12. The functional tips 16 may preferably have a slightly spread wishbone configuration that has a mild curvature to the two arms of the wishbone, and may be of any configuration depending on the intended use of the device, e.g. needle holder, scissors, grasper, etc.

The proximal end 22 of the light pipe 12 forms the connector that attaches to the light source 20 used to illuminate the device. The proximal end 22 may take many forms. For example, it may be threaded for quick connection to a reusable handle portion employing a fiberoptic cable, or it may have a bayonette configuration 24 enabling it to use currently available light emitting diode (LED) light sources. Towards the proximal end of the light pipe is a collar 26 molded into the light pipe 12 that serves to anchor the proximal end of the sliding closure sleeve 14. Also preferably molded into the light pipe 12 are two anti-rotation members 28 that also serve as stops to prevent the closure sleeve 14 from overextending.

The sliding closure sleeve 14 forms the basis of the closure mechanism of the device 10. Several configurations are possible. In one embodiment, the sliding closure sleeve 14 is molded in two halves and encases the light pipe 12 and is bonded or welded together. The top portion of the sleeve 14 fits into the 26 collar on the upper end of the light pipe 12; when assembled, the collar 26 fixes the upper end of the sleeve 14 and prevents it from moving. The next portions of the sleeve 14 are the two finger grips 30. These have a spring-like action; squeezing the finger grips 30 acts to displace the sliding sleeve 14 distally. Since the upper end of the sleeve 14 is fixed by the collar 26 on the light pipe 12, the sleeve 14 can only slide distally, toward the functional tips 16. As the sleeve 14 slides over the functional tips 16, they are forced together in opposition, eventually meeting and closing. The light pipe body 12 has anti-rotation/stop members 28 that serve both to prevent the sleeve from spinning about the light pipe 12, and also to limit the distal movement of the sleeve 14. This prevents the sleeve 14 from overly compressing and possibly deforming the functional tips 16.

In another embodiment, the light pipe 12 and sliding closure sleeve 14 are intended to be used with a detachable, reusable handle portion (not shown). In this configuration, the proximal end of the light pipe is threaded or otherwise mates securely with the handle portion. The sliding closure sleeve is assembled over the light pipe and kept in place by the collar 26 and/or the anti-rotation nubs 28. Other mechanisms of functionally similar design may also be used to keep the closure sleeve in place. In this embodiment, action from the handle portion forces the sliding closure sleeve distally where it causes closure of the functional tips by forcing them together in opposition as it slides over the spread arms of the functional tips.

The closure mechanism as described provides several key benefits. First, the light pipe is molded in a single piece, providing a clear and unobstructed light path from the light source to the functional tips, minimizing light loss. This should provide maximum transmission of light onto the procedure site, improving illumination and visualization.

Next, since the device is molded from plastic, mechanical stresses during use can be potential failure modes. To prevent this, although the plastic light pipe is relatively narrow, it is held in tension as the foreign body remover is used. This means that it will not bow, bend or buckle due to compressive force during use. The sliding sleeve is in compression during use, but is mechanically a more structurally stable piece. This arrangement ensures safe, secure operation of the device. Also, the distance from the end of the sliding sleeve to the end of the functional tips is kept short, reducing the lever-arm length and ensuring adequate stiffness and strength of the functional tips as they close.

A final benefit of the mechanism used to operate the device is seen in the embodiment where the handle portion is permanently affixed to the light pipe portion. In this configuration, the light pipe is prevented from moving backward away from the procedure site during operation by the fixation of the upper end of the squeezable handle into the collar molded into the body of the light pipe. This is important, as it allows the user to accurately position the functional tips at the operative site and be confident that the relative positions of the functional tips and procedure site will not change as the tips are closed.

Referring specifically to the drawings, FIG. 1 shows a side view of a light transmitting medical instrument 10 in accordance with the invention. One side of the sliding closure sleeve 14 is seen, with the actuator finger grips 30, the collar 26 for fixating the finger grips 30, and the anti-rotation/stop member 28 shown. The functional arms 16 which comprise that distal tip of the light pipe 12 are shown. The light pipe 12 is shown with a male bayonet connector 24 at its proximal end intended to be inserted into and locked onto an LED light source 20.

Figure 2:
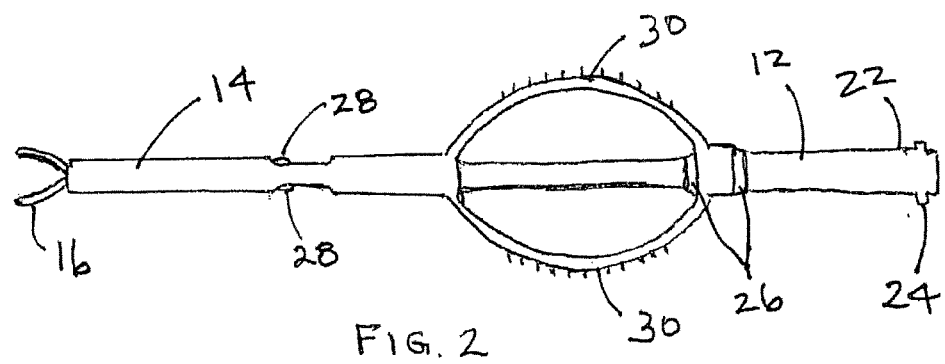
FIG. 2 shows a top view of the light transmitting medical instrument of FIG. 1.

FIG. 2 shows the light transmitting medical instrument 10 in a top view. In this view, the positional relation of the sliding sleeve 14 and the light pipe 12 is clearly seen. The actuator finger grips 30 and the collar 26 for fixating the upper end of the sliding sleeve 14 are also shown. At the distal end of the light pipe 12, the functional tip 16 can be seen as it extends past the sliding closure sleeve 14.

Figure 3:
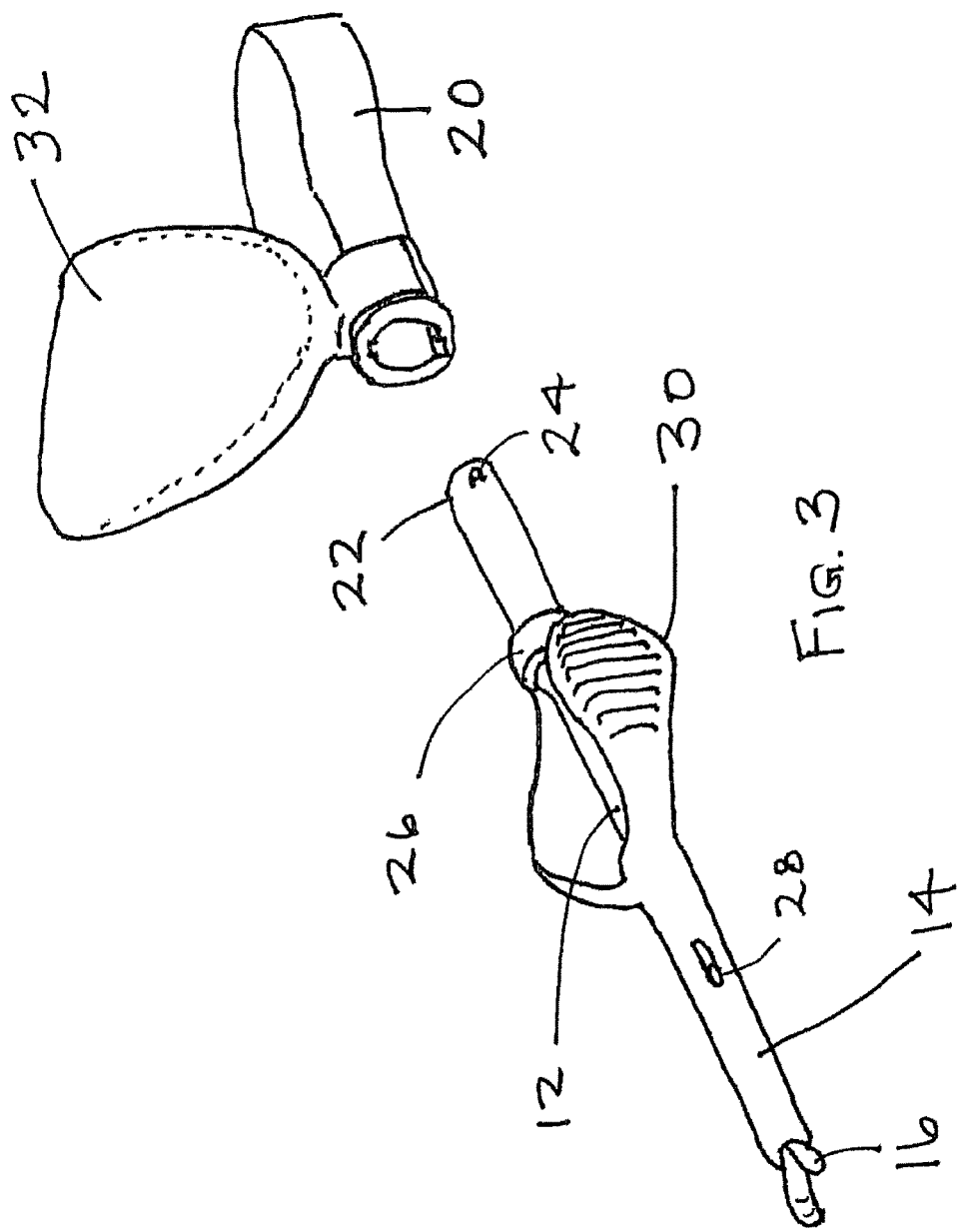
FIG. 3 shows an enlarged, isometric view of the light transmitting medical instrument of FIG. 1 and a light source and magnification lens for use therewith.

FIG. 3 shows an isometric view of the light transmitting medical instrument 10. Also shown is an LED light source 20, intended to accept the male bayonet connector 24 at the proximal end of the light pipe 12, and a magnification lens 32 to enhance operator visualization.

Figure 4:
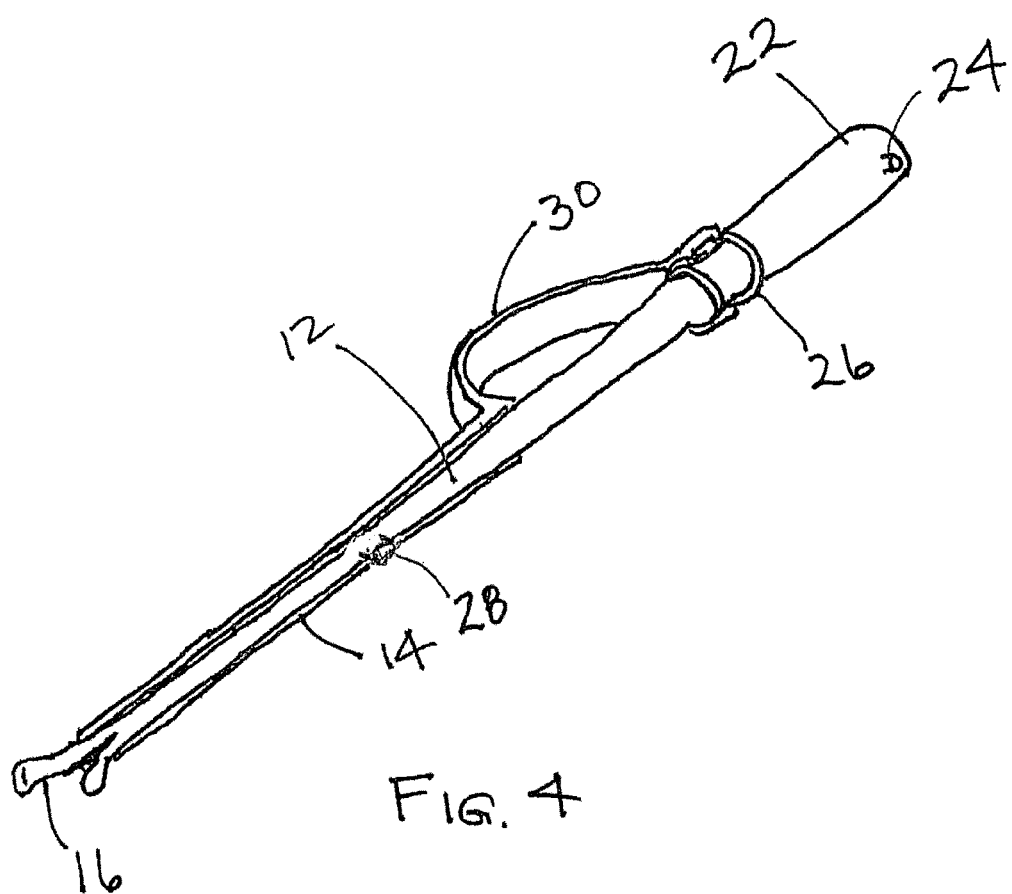
FIG. 4 shows the same isometric view of the foreign body remover as in FIG. 3, but with portions broken away.

FIG. 4 shows the same isometric view of the foreign body remover 10 as in FIG. 3, but with one half of the sliding sleeve 14 removed in order to show the internal working relationships of the light pipe 12 and the sliding sleeve 14. Additionally, the LED light source is not shown. With one half of the sliding sleeve removed 14, the internal relationship of the light pipe 12 and the sliding sleeve 14 is clearly seen. The light pipe 12 extends as a solid, unbroken rod from the bayonet attachment 24 at the proximal end to the functional tip 16, providing a clear light path for maximum illumination. Molded into the light pipe 12 is the collar 26 for fixating the upper end of the sliding sleeve 14 and finger grip 30. Also molded into the light pipe 12 is the anti-rotation/stop member 28 that prevents the sleeve 14 from rotating about the light pipe 12 and keeps the sliding sleeve 14 from over-extending over the functional tip 16. The segments of the sliding closure sleeve 14—upper end fixated to the light pipe collar 26, actuator finger grip 30, and the body of the sliding sleeve extending to the functional tip 16—are clearly seen. When the actuator finger grips 30 are squeezed, because they are fixed at the collar 26 on the light pipe 12 at the upper end, the squeezing action forces the sliding closure sleeve down 14 onto the upper portion of the functional tip arms 16. This, in turn, causes the functional tip arms 16 to close and meet.

Figure 5:
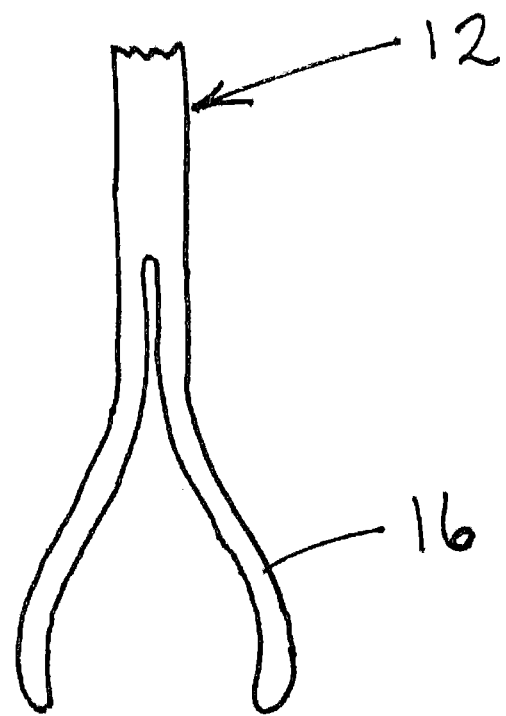
FIG. 5 shows a close-up, top view of the functional tip arms.

FIG. 5 shows a close-up view of the functional tip arms 16. The functional tip arms 16 are shown in a "wishbone" like configuration that allows the arms to flex inward as the sliding closure sleeve 14 moves down over them, effecting closure of the functional tip 16. Distal movement of the sliding closure sleeve 14 over the spread curvature of the functional tip arms 16 causes them to close firmly and securely.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A light transmitting medical instrument, comprising:
   a light pipe having a first end operatively coupled to a light source and a second end defining a functional tip having at least two arms, the light pipe being molded in a single piece, providing a clear and unobstructed light path from the light source to each of the at least two arms of the functional tip; and a sliding closure sleeve mounted about the light pipe, the sliding closure sleeve having a first end portion at which the sliding closure sleeve is fixed to the light pipe in a manner such that relative movement therebetween is prevented and a second end proximate the functional tip of the light pipe, the sliding closure sleeve further comprising actuator grips that consist of a single pair of spring-like actuator finger grips that, when forced radially inward one toward the other, causes the second end of the sliding closure sleeve to move toward the functional tip, thereby forcing the arms of the functional tip towards one another.

2. The light transmitting medical instrument of claim 1, wherein said light source is an LED light source.

3. The light transmitting medical instrument of claim 1, wherein said light pipe is comprised of a transparent plastic.

4. The light transmitting medical instrument of claim 1, wherein said light pipe is comprised of a transparent polycarbonate plastic.

5. The light transmitting medical instrument of claim 1, further comprising an anti-rotation mechanism comprised of a stop molded as part of the light pipe that mates to a recess in the sliding closure sleeve to prevent the sliding closure sleeve from rotating on the light pipe and limits the distal movement of the sliding closure sleeve down the light pipe to prevent over-extension of the sliding closure sleeve.

6. The light transmitting medical instrument of claim 1, further comprising a collar on the sliding closure sleeve that mates with a collar that is monolithic with the light pipe to fix the position of the upper end of the sliding closure sleeve on the light pipe.

7. The light transmitting medical instrument of claim 1, wherein the light pipe extends as a solid, unbroken rod from the first end to second end, and the first end portion of the sliding closure sleeve extends about and is fixed to the light pipe proximate the first end of the light pipe.

8. A light transmitting medical instrument, comprising:
a light pipe having a first end operatively coupled to a light source and a second end having a functional tip having at least two arms, the light pipe being molded in a single piece, providing a clear and unobstructed light path from the light source to each of the at least two arms of the functional tip, the first end of the light pipe having a bayonet connector that is monolithic with the light pipe, the bayonet connector being configured to be inserted into and locked onto the light source; and a sliding closure sleeve mounted about the light pipe, the sliding closure sleeve having a first end portion at which the sliding closure sleeve is fixed to the light pipe in a manner such that relative movement therebetween is prevented and a second end proximate the functional tip of the light pipe, the sliding closure sleeve further comprising a spring-like actuator finger grip that, when forced radially inward, causes the second end of the sliding closure sleeve to move toward the functional tip, thereby forcing the arms of the functional tip towards one another.

9. The light transmitting medical instrument of claim 8, wherein said light source is an LED light source.

10. The light transmitting medical instrument of claim 8, wherein said light pipe is comprised of a transparent plastic.

11. The light transmitting medical instrument of claim 8, wherein said light pipe is comprised of a transparent polycarbonate plastic.

12. The light transmitting medical instrument of claim 8, further comprising an anti-rotation mechanism comprised of a stop molded as part of the light pipe that mates to a recess in the sliding closure sleeve to prevent the sliding closure sleeve from rotating on the light pipe and limits the distal movement of the sliding closure sleeve down the light pipe to prevent over-extension of the sliding closure sleeve.

13. The light transmitting medical instrument of claim 8, further comprising a collar on the sliding closure sleeve that mates with a collar that is monolithic with the light pipe to fix the position of the upper end of the sliding closure sleeve on the light pipe.

14. The light transmitting medical instrument of claim 8, wherein the light pipe extends as a solid, unbroken rod from the first end to second end, and the first end portion of the sliding closure sleeve extends about and is fixed to the light pipe proximate the first end of the light pipe.

* * * * *